United States Patent
Vanhessche et al.

(10) Patent No.: US 9,090,533 B2
(45) Date of Patent: Jul. 28, 2015

(54) PROCESS FOR PRODUCING 4-CYCLOHEXYL-2-METHYL-2-BUTANOL

(71) Applicant: FIRMENICH SA, Geneva (CH)

(72) Inventors: Koenraad P. Vanhessche, Feigeres (FR); Jean-Paul Leresche, Arbaz (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 14/411,490

(22) PCT Filed: Jun. 24, 2013

(86) PCT No.: PCT/EP2013/063159
§ 371 (c)(1),
(2) Date: Dec. 27, 2014

(87) PCT Pub. No.: WO2014/001266
PCT Pub. Date: Jan. 3, 2014

(65) Prior Publication Data
US 2015/0158798 A1    Jun. 11, 2015

Related U.S. Application Data

(60) Provisional application No. 61/664,982, filed on Jun. 27, 2012.

(30) Foreign Application Priority Data

Jul. 26, 2012 (EP) .................................. 12178003

(51) Int. Cl.
*C07C 29/132* (2006.01)
*C07C 29/60* (2006.01)
*C07C 29/20* (2006.01)

(52) U.S. Cl.
CPC ............... *C07C 29/132* (2013.01); *C07C 29/20* (2013.01); *C07C 29/60* (2013.01); *C07C 2101/14* (2013.01)

(58) Field of Classification Search
CPC .............................. C07C 29/132; C07C 29/60
See application file for complete search history.

(56) References Cited

U.S. PATENT DOCUMENTS

| 2,689,870 | A | * | 9/1954 | Steadman ...................... 568/814 |
| 2,700,685 | A | * | 1/1955 | Cooper et al. ................ 568/865 |
| 3,338,842 | A | | 8/1967 | Beaird et al. |
| 4,701,278 | A | | 10/1987 | Fehr |
| 5,053,559 | A | * | 10/1991 | Jefford .......................... 568/814 |
| 8,450,534 | B2 | | 5/2013 | Ebel et al. |
| 2011/0237684 | A1 | | 9/2011 | Ebel et al. |

FOREIGN PATENT DOCUMENTS

WO    WO2011117360    9/2011

OTHER PUBLICATIONS

International Search Report and Written Opinion, application PCT/EP2013/063159, mailed Aug. 12, 2013.
Dyson P. J., Arene hydrogenation by homogenous catalyst—fact or fiction, Dalton Trans., 2003, 2964-2974.
El Gharbi et al., Synthesis, G.T. Verlag, vol. 5, 1981, 361-362.
Herscovici et al., Revista de Chimie, vol. 14, n° 8, 1963, 447-450.
John Matthey Catalysts Handbook of Pharmaceutical Catalysis, section 4.1.2, pp. 23-25 (2009).
Kataoka et al., Journal of Organic Chemistry, 1997, 62, 8109-8113.
Kochi, Journal of Organic Chemistry, 1963, vol. 28, 1960-1968.
Okazawa et al, Can. J. Chem., 60, 2180-93 (1982).
Oriyama et al., Synthetic Communic., vol. 31, n° 15, 2001, 2305-2311.
Searles, Scott, Jr. et al., "Base-Catalyzed Cleavage of 1,3-Diols," Dept. of Chemistry, Kansas State College, Manhattan, Kan., 1770-1775 (Oct. 6, 1958).

* cited by examiner

*Primary Examiner* — Brian J Davis
(74) *Attorney, Agent, or Firm* — Winston & Strawn LLP

(57) ABSTRACT

The present invention relates to the field of perfumery. More particularly, it concerns a process for the preparation of 2-methyl-4-phenyl-2-butanol, or even 4-cyclohexyl-2-methyl-2-butanol from 4,4-dimethyl-2,6-diphenyl-1,3-dioxane.

10 Claims, No Drawings

PROCESS FOR PRODUCING 4-CYCLOHEXYL-2-METHYL-2-BUTANOL

TECHNICAL FIELD

The present invention relates to the field of perfumery. More particularly, it concerns a process for the preparation of 2-methyl-4-phenyl-2-butanol, or even 4-cyclohexyl-2-methyl-2-butanol from 4,4-dimethyl-2,6-diphenyl-1,3-dioxane.

PRIOR ART

2-Methyl-4-phenyl-2-butanol, or even 4-cyclohexyl-2-methyl-2-butanol are priced perfumery ingredients.

In particular 4-cyclohexyl-2-methyl-2-butanol, is a fragrance with a lily-of the-valley odor that is used in the preparation of perfumes and perfumed materials. 4-cyclohexyl-2-methyl-2-butanol was taught, as a chemical compound, by N. E. Okazawa et al. [Can. J. Chem., 60, 2180-93(1982). Okazawa describes a process for preparing 4-cyclohexyl-2-methyl-2-butanol that includes the conversion of 3-cyclohexylpropanoic acid to the acid chloride, which is then reacted with 2 mol of methyl lithium to give 4-cyclohexyl-2-methyl-2-butanol. When produced on a large scale, however, this process is economically unattractive and is afflicted with the risk of using methyl lithium.

U.S. Pat. No. 4,701,278 describes 4-cyclohexyl-2-methyl-2-butanol fragrance properties and its use in both fine and technical perfumery. This patent is expressly incorporated herein by reference thereto for the purpose of understanding the properties and uses of 4-cyclohexyl-2-methyl-2-butanol.

Kochi. 1963. Journal of Organic Chemistry. (1963) 28, 1960. describes a process for the preparation 4-phenyl-2-methyl-2-butanol via a radical coupling of styrene and acetone. Such a process is not well suited for industrial purposes since carrying out such radical chemistry requires strict conditions and produces significant amounts of by-product, thus lowering the global yield of the desired product.

Kataoka et al. Journal of Organic Chemistry. (1997) 62, 8109 describes a process for the preparation 4-phenyl-2-methyl-2-butanol via a Grignard reaction over 4-phenyl-butan-2-one. Such a process is not well suited for industrial purpose since using expensive reagents such as a Grignard one.

Ebel et al., U.S. Patent Publication 2011/0237684, describes a process for preparing 4-cyclohexyl-2-methyl-2-butanol or 2-methyl-4-phenyl-2-butanol involving reacting styrene with isopropanol at an elevated temperature of 250-500° C. to obtain 4-phenyl-2-methyl-2-butanol, followed by heterogeneously catalyzing the hydrogenation of 4-phenyl-2-methyl-2-butanol over a catalyst suitable for ring hydrogenation of aromatics. This method requires careful precautions to avoid the self-polymerization of styrene.

Accordingly, there is a need for improved processes for making 4-cyclohexyl-2-methyl-2-butanol or 2-methyl-4-phenyl-2-butanol that are not subject to the disadvantages of the prior art. These are now provided by the present invention.

SUMMARY OF THE INVENTION

We have now surprisingly discovered that 4-cyclohexyl-2-methyl-2-butanol can be advantageously obtained from 4,4-dimethyl-2,6-diphenyl-1,3-dioxane (DDD) for example, either via the intermediate compound, 2-methyl-4-phenyl-2-butanol (also known as Carbinol Muguet or CM) or via two intermediate compounds, 2-methyl-4-phenyl-2,4-butanediol (HCM) and CM.

The process of producing 4-cyclohexyl-2-methyl-2-butanol according to the present invention has several advantages. It can be conducted using readily available starting materials, under relatively straightforward conditions without generating undesirable byproducts, in high yield and avoiding the use of hazardous radical chemistry.

DESCRIPTION OF THE INVENTION

The present invention provides the use of 4,4-dimethyl-2, 6-diphenyl-1,3-dioxane (DDD) to produce 2-methyl-4-phenyl-2-butanol (CM). In other words, the present invention provides a process for the conversion of 4,4-dimethyl-2,6-diphenyl-1,3-dioxane (DDD) into 2-methyl-4-phenyl-2-butanol (CM).

According to an embodiment of the invention, said conversion can be achieved by:
- the hydrogenolysis of 4,4-dimethyl-2,6-diphenyl-1,3-dioxane (DDD) to produce directly 2-methyl-4-phenyl-2-butanol (CM); or
- a) the hydrolysis of DDD to 2-methyl-4-phenyl-2,4-butanediol (HCM); and
- b) the hydrogenolysis of 2-methyl-4-phenyl-2,4-butanediol (HCM) into 2-methyl-4-phenyl-2-butanol (CM).

The starting material DDD is known form the prior art and can be prepared isobutylene and benzaldehyde utilizing processes previously described (see, e.g., Revistate Chemica. 1963, 14(8), 447). According to an embodiment of the invention, the invention's process further comprises the below step for preparing the starting material, or in other words its use as starting material prepared as described below. Indeed, the production of DDD can be improved. Therefore, according to an embodiment of the above invention, the invention process can further comprise a step for the preparation of DDD, wherein isobutylene and benzaldehyde are reacted in the presence of a Lewis acid instead of a protic acid (as in the prior art) to significantly enhance the yield of DDD to 90%.

According to a particular aspect of this embodiment, the Lewis acid is advantageously selected amongst $BF_3$, a $BF_3$ adducts with $C_{2-4}$ ether or carboxylic acids (such as $BF_3(OEt_2)_2$ or $BF_3(AcOH)_2$) or $FeCl_3$, the latter being preferably in an anhydrous form. The amount of Lewis acid used in the process can be advantageously comprised between about 0.1% to about 5%, or even between about 0.5% to about 3%, percentage being relative to the molar amount of isobutylene.

According to a particular aspect of this embodiment, the preferred molar ratio of benzaldehyde to isobutylene is from about 2:1 to 6:1, and a more preferred ratio is from about 3:1 to 4:1.

According to a particular aspect of this embodiment, the temperature range of the reaction is from about 0° C. to 80° C., more preferably from about 20° C. to 50° C. and more preferably at about 40° C.

As mentioned above, according to an embodiment of the invention, the conversion of 4,4-dimethyl-2,6-diphenyl-1,3-dioxane (DDD) into 2-methyl-4-phenyl-2-butanol (CM), can be achieved by the hydrogenolysis of DDD to produce directly Carbinol Muguet (CM).

According to said embodiment, the hydrogenolysis is carried out in the presence of a hydrogenation catalyst. The hydrogenolysis can be performed using purified DDD or using neutralized crude DDD.

According to any invention's embodiments, and in particular, the catalyst for the hydrogenolysis of DDD into CM includes but is not limited to supported Pd but other transition metal catalysts can be used. Typical and limiting examples are Pd/C, $Pd/BaSO_4$, $Pd/Al_2O_3$, $Rh/Al_2O_3$ (for supported Pd and Rh: typically 2 to 20% w/w of metal relative to the total weight of catalyst (i.e. metal+support)) and Raney Ni. According to a particular embodiment the catalyst is Pd/C. The amount of catalyst for the hydrogenolysis used in the process can be advantageously comprised between about 0.3% to about 5%, or even between about 0.5% to about 3%, percentage being relative to the weight of DDD.

Optionally, in the hydrogenolysis a protic acid may be used, preferably in the range of about 0 to 5% by weight compared to DDD and more preferably in the range of about 0 to 3.0%. Typical but non-limiting example of protic acids are $H_3PO_4$, $H_2SO_4$, or a $C_1$-$C_{10}$ sulfonic acid such as methane sulfonic acid, camphor sulfonic acid or p-toleune sulfonic acid.

The hydrogenolysis can be carried out at a temperature range of about 50° C. to about 150° C., preferably at a range of about 60° C. to about 120° C.

The hydrogenolysis can be carried out at a $H_2$ pressure of about 1 to about 50 Bar, preferably about 2 to about 20 Bar.

Moreover the hydrogenolysis of DDD can be carried out in the presence or in the absence of a solvent or diluent. Suitable solvents include $C_{1-4}$ alcohols, $C_{3-8}$ esters, $C_{4-8}$ ethers, $C_{6-10}$ hydrocarbons and in an amount of up to 100% by weight compared to DDD. Useful solvents or diluents are in principle those which are capable of very substantially dissolving the organic compounds to be hydrogenolyzed, or mix completely therewith, and which are inert under the hydrogenolysis conditions, i.e. are not hydrolysed. Examples of suitable solvents include MeOH, EtOH or $^i$PrOH, EtOAc, BuOAc, THF toluene and heptanes.

As mentioned above, according to an embodiment of the invention, in an alternative to the previous hydrogenolysis process, the conversion of 4,4-dimethyl-2,6-diphenyl-1,3-dioxane (DDD) into 2-methyl-4-phenyl-2-butanol (CM) can be achieved by a process comprising:
i. the hydrolysis of DDD to 2-methyl-4-phenyl-2,4-butanediol (HCM); and
ii. the hydrogenolysis of 2-methyl-4-phenyl-2,4-butanediol (HCM) into 2-methyl-4-phenyl-2-butanol (CM).

The hydrolysis of DDD to HCM can be carried out in a high pressure reactor charged with DDD and deionized water. The hydrolysis can by performed at a temperature comprised between about 100° C. and about 250° C., or even comprised between about 180° C. and about 220° C. The pressure of the reaction medium during the hydrolysis can be comprised between about 1 bar and about 50 bars, or even between about 5 bar and about 20 bars.

According to a particular aspect of this embodiment, the hydrolysis can be carried out in the presence of a small amount of a weak base such as $Na_2CO_3$, $NaHCO_3$ or $Na_3PO_4$. Typically, the weak base can be used in an amount comprised between about 0.02% to about 0.2%, or even between about 0.05% to about 0.1%, percentage being relative to the weight of DDD.

The hydrolysis reaction is quite surprising since S. Searles et al, in *J. Org. Chem.*, 1959, 24, 1770, showed that in general similar 1,3-diol under such superheated condition decomposes quite seriously. Similar decomposition was also observed during hydrolysis of DDD under classic aqueous acidic conditions (e.g. HOAc, dilute HCl, $H_2SO_4$, . . . ), but not when carried out under the above-described superheated conditions.

The hydrogenolysis of HCM into 2-methyl-4-phenyl-2-butanol (CM) can be carried out in the presence of any catalyst known to perform the reduction of a benzylic alcohol into the corresponding toluene derivative. One may use the same catalyst listed above for the hydrogenolysis of DDD. As non limiting example one may cite as catalysts Pd/C catalyst (typically 2 to 10% w/w of Pd relative to the total weight of Pd/C).

The hydrogenolysis of HCM can by performed at a temperature comprised between about 50° C. and about 150° C., or even comprised between about 70° C. and about 110° C. The pressure of the reaction medium during the hydrogenolysis of HCM can be comprised between about 1 bar and about 50 bars, or even comprised between about 8 bar and about 20 bars.

Advantageously, this alternative embodiment can be carried out in two subsequent steps or directly as a "one-pot" process.

The CM thus obtained can be suitably used as an aroma chemical, or as substrate for the hydrogenation to 4-cyclohexyl-2-methyl-2-butanol. Indeed, the invention's process can also advantageously be used to further produce 4-cyclohexyl-2-methyl-2-butanol, another valuable perfuming ingredient. Therefore the invention further comprises as additional embodiment the invention's process further comprising the conversion of CM into 4-cyclohexyl-2-methyl-2-butanol, or in other words a process as follows:
a) converting 4,4-dimethyl-2,6-diphenyl-1,3-dioxane (DDD) to 2-methyl-4-phenyl-2-butanol (CM), as mentioned above; and
b) hydrogenating the 2-methyl-4-phenyl-2-butanol (CM) under conditions sufficient to produce 4-cyclohexyl-2-methyl-2-butanol.

According to said embodiment, the CM obtained by the invention process can be further hydrogenated to produce 4-cyclohexyl-2-methyl-2-butanol. The reduction of a benzene ring into a cyclohexane ring is a reaction well known to a person skilled in the art. The hydrogenation of CM to 4-cyclohexyl-2-methyl-2-butanol can be done in the presence of a supported catalyst such as $Ru/Al_2O_3$ (typically 2 to 10% w/w of Ru relative to the total weight of $Ru/Al_2O_3$). Other possible catalysts are Rh/C, Ru/C or Pt/C (typically 2 to 10% w/w of metal relative to the total weight of metal and support).

A person skilled in the art recognizes that other non-poisoned Ruthenium-based heterogeneous catalysts may be used. Catalysts for the hydrogenation of arene into saturated rings are described in Dyson, P. J. *Arene hydrogenation by homogenous catalysts: fact or fiction*?. Dalton Trans. 2003, 2964-2974. In Table 1 for example. And also in John Matthey Catalysts. Handbook of Pharmaceutical Catalysis. For example, pages 23 and 24 or section 4.1.2.

This hydrogenation can be effected at a hydrogen pressure of 1-50 bars, preferably from 5-30 bars. This hydrogenation can be effected at a temperature range of 50-120° C., preferably at a range of 60-105° C., more preferably at a range of 60 to 95° C. A skilled in the art recognizes that the hydrogenation process can be performed in the absence of a solvent or diluents and in the presence of a solvent or diluents. For example, a solvent miscible with CM and inert under $H_2$ may be used. Useful solvents or diluents are in principle those which are capable of very substantially dissolving the organic compounds to be hydrogenated, or mix completely therewith, and which are inert under the hydrogenation conditions, i.e. are not hydrolyzed. Examples of suitable solvents can be a $C_{1-4}$ alcohol such as MeOH or iPrOH.

EXAMPLES

The invention will now be described in further detail by way of the following examples, wherein the abbreviations have the usual meaning in the art, the temperatures are indicated in degrees centigrade (° C.); the NMR spectral data were recorded in CDCl$_3$ (if not stated otherwise) with a 360 or 400 MHz machine for $^1$H and $^{13}$C, the chemical shifts are indicated in ppm with respect to TMS as standard, the coupling constants J are expressed in Hz.

Example 1

Synthesis of 4,4-dimethyl-2,6-diphenyl-1,3-dioxane (DDD) from isobutylene and benzaldenhyde A 2 L 4-neck round bottom flask equipped with a reflux condenser, magnetic stir bar and thermometer was placed under nitrogen atmosphere and charged with 7.84 g of BF$_3$OEt$_2$ (0.055 mol, 0.01 molar equivalents) and 1044 g of benzaldehyde (9.84 mol, 2 molar equivalents). The mixture was heated to 40° C. with good agitation and then introduced with 278 g of isobutylene (4.95 mol, 1 molar equivalents) over a 2 hours period, never allowing the reaction temperature to rise above 46° C. throughout the addition. The reaction is then stirred for an additional 3 hours at 40° C. and quenched with 30 mL of 10% aqueous Na$_2$CO$_3$. The temperature is then raised to 60° C. and if the pH is neutral, the reaction mixture is charged with 90 mL of 15% Na$_2$SO$_4$, stirred for an additional 10 minutes and phase separated. Another wash with 90 mL of 15% aqueous Na$_2$SO$_4$ is performed and after phase separation, 1257 g of crude organic reaction mixture is obtained. The latter is then topped to remove excess benzaldehyde and then gradually increasing both the vacuum and pot temperature to 1.4 Torr and 130° C., respectively, leading to an liquid that solidifies upon cooling to <75° C. The crude DDD is then taken on to the next step without further purification. (The crude DDD can be distilled at a pot temperature of 125-130° C. at 0.2 mbar). According to internal standard analysis, the molar yield DDD is 70% based on isobutylene.

Using a molar ratio of benzaldehyde isobutylene of 3/1, DDD was obtained with a molar yield of 90% based on isobutylene.

Other Lewis acids were also tested such as BF$_3$(AcOH)$_2$, which gave a similar yield to that of BF$_3$OEt$_2$ and FeCl$_3$, which gave a 78% molar yield for DDD based on isobutylene. The use of FeCl$_3$, however necessitated a stainless steel reactor as well as multiple washes to pacify the material or distillation of the crude DDD.

Example 2

Hydrogenolysis of DDD (4,4-dimethyl-2,6-diphenyl-1,3-dioxane) to CM (2-methyl-4-phenyl-2-butanol)

In a 6 liter high pressure reactor (autoclave) where charged 4100 g DDD, 20.5 g of 5% Pd/C catalyst (50% wet), and 16.4 g of 85% H$_3$PO$_4$. The reactor was closed, sealed, vacuumed and purged 3 times with N$_2$ at 4 bar. Then, it was vacuumed and filled with pressurized hydrogen to 10 bar. This procedure was repeated twice. Then, under stirring, hydrogen pressure was increased to 15 bar, and temperature gradually raised to 80° C. Hydrogenation had been run for a total of 36 hours at 80-105° C., after which the reaction was cooled down to 80° C. and filtered from the catalyst. The aqueous phase was withdrawn and the organic phase washed from the residual acid with a NaHCO$_3$ solution.

Washed organic phase was charged into the fractionating still. After toluene was removed at slight vacuum (~250 mbar), the remainder of the material was distilled at progressively increasing vacuum (up to 2 mbar eventually) and vapor temperature 60-80° C., recovering a total of 1800 g of CM. It was suitable for the use as aroma chemical, or for further hydrogenation processes.

Example 3

Hydrolysis of DDD (4,4-dimethyl-2,6-diphenyl-1,3-dioxane) to 2-methyl-4-phenyl-2,4-butanediol (HCM)

A 300 ml high pressure reactor (autoclave) was charged with 77.9 g DDD and 34.2 g of 0.07% solution of Na$_2$CO$_3$ in water. Reactor was closed, sealed, vacuumed and purged with N$_2$. Then, under stirring, temperature was gradually raised to 200° C. and kept at 200° C. for 4.5 hours; at that point, the pressure inside the autoclave was approximately 16 bar. Then reactor was cooled down, and its contents discharged. The organic phase contained (area % GC) 43.4% benzaldehyde, 37.4% HCM, and 6.7% unreacted DDD.

Example 4

Hydrolysis of DDD (4,4-dimethyl-2,6-diphenyl-1,3-dioxane) to 2-methyl-4-phenyl-2,4-butanediol (HCM) and HCM hydrogenolysis to 2-methyl-4-phenyl-2-butanol A 450 ml high pressure reactor (autoclave) was charged with 72 g DDD and 74.5 g of deionized water had been charged. Reactor was closed, sealed, vacuumed and purged with N$_2$. Then, under stirring, temperature was gradually raised to 200° C. and kept at 200° C. for 2.5 hours. At that point, the pressure inside the autoclave was approximately 15 bar. Then reactor was cooled down, and its contents discharged. The organic phase was separated from the aqueous phase and flash distilled under vacuum. Distilled material was fractionated in vacuum on a packed distillation column to recover benzaldehyde and to deliver a crude HCM. 73.8 g of the crude HCM together with 0.36 g of 5% Pd/carbon catalyst (50% moist) were charged into the cleaned and dried autoclave. The reactor was purged 3 times with N$_2$, then 3 times with hydrogen. Under stirring the hydrogen pressure was brought to 14 bar and the temperature to 90° C. After 5 hours, the reactor was cooled down and its contents analyzed. The reaction mix contained (area % GC) 92% CMt (CM), 0.3% HCM, and 4.8% toluene. The reaction mix was then filtered from the catalyst and fractionally distilled to produce olfactively acceptable CM.

Example 5

Hydrogenation of CM to 4-cyclohexyl-2-methyl-2-butanol

6 Liter high-pressure stirred reactor (Parr Engineering) was charged with 4100 grams of CM and 14 grams of 5% Ru/Al$_2$O$_3$ catalyst. Reactor was closed, then vacuumed and pressurized with nitrogen to 3 bar. Then, the pressure was vented and the vacuum was broken with hydrogen and the reactor was pressurized to 5 bar. Under stirring, the reactor was pressurized with hydrogen to 14 bar. Temperature was raised to 60° C. Hydrogenation was run for 8 hours at 60-90° C. and 14 bar. At this point, GC analysis showed the residual content of CM of 0.12%.

The reaction mix was filtered from the catalyst and distilled on a fractionating column, resulting in 3900 g olfactively acceptable 4-cyclohexyl-2-methyl-2-butanol.

What is claimed is:

1. A process for the preparation of 2-methyl-4-phenyl-2-butanol comprising:

the hydrogenolysis of 4,4-dimethyl-2,6-diphenyl-1,3-dioxane to produce 2-methyl-4-phenyl-2-butanol; or a) the hydrolysis of 4,4-dimetliyl-2,6-diphenyl-1,3-dioxane to 2-methyl-4-phenyl-2,4-butanediol; and b) the hydrogenolysis of 2-methyl-4-phenyl-2,4-butanediol to produce 2-methyl-4-phenyl-2-butanol.

2. A process according to claim 1, wherein the hydrogenolysis is carried out in the presence of Pd/C.

3. A process according to claim 1, wherein the hydrolysis is carried out in the presence of deionized water and $Na_2CO_3$ in a high pressure reactor.

4. A process according to claim 1, wherein the 4,4-dimethyl-2,6-diphenyl-1,3-dioxane is previously obtained by a process comprising the reaction of isobutylene and benzaldehyde in the presence of a Lewis acid.

5. A process according to claim 4, wherein said Lewis acid is $BF_3$, a $BF_3$ adduct with $C_{2-4}$ ether or carboxylic acids, or $FeCl_3$.

6. A process as recited in claim 1 for the preparation of 4-cyclohexyl-2-methyl-2-butanol comprising hydrogenating the 2-methyl-4-phenyl-2-butanol to produce 4-cyclohexyl-2-methyl-2-butanol.

7. A process as recited in claim 2 for the preparation of 4-cyclohexyl-2-methyl-2-butanol comprising hydrogenating the 2-methyl-4-phenyl-2-butanol to produce 4-cyclohexyl-2-methyl-2-butanol.

8. A process as recited in claim 3 for the preparation of 4-cyclohexyl-2-methyl-2-butanol comprising hydrogenating the 2-methyl-4-phenyl-2-butanol to produce 4-cyclohexyl-2-methyl-2-butanol.

9. A process as recited in claim 4 for the preparation of 4-cyclohexyl-2-methyl-2-butanol comprising hydrogenating the 2-methyl-4-phenyl-2-butanol to produce 4-cyclohexyl-2-methyl-2-butanol.

10. A process as recited in claim 5 for the preparation of 4-cyclohexyl-2-methyl-2-butanol comprising hydrogenating the 2-methyl-4-phenyl-2-butanol to produce 4-cyclohexyl-2-methyl-2-butanol.

* * * * *